United States Patent [19]

Stasz et al.

[11] 4,386,634
[45] Jun. 7, 1983

[54] PROPORTIONING SYSTEM

[75] Inventors: Peter Stasz, Minneapolis; Louis C. Cosentino, Wayzata, both of Minn.

[73] Assignee: Renal Systems, Inc., Minneapolis, Minn.

[21] Appl. No.: 195,796

[22] Filed: Oct. 10, 1980

[51] Int. Cl.³ .............................................. B65B 3/04
[52] U.S. Cl. .......................................... 141/2; 141/9; 141/10; 141/67; 141/105; 141/114; 222/386.5; 222/630; 366/189
[58] Field of Search ................. 222/630, 386.5; 141/9, 141/10, 114, 105, 67, 313–317, 1–8, 11, 12; 366/184, 189, 191

[56] References Cited

U.S. PATENT DOCUMENTS 3,515,275 6/1970 Bowman .
3,799,873 3/1974 Brown .
3,878,095 4/1975 Frasier et al. .
4,037,616 7/1977 Pinkerton .
4,193,515 3/1980 Purdy .................................. 141/105
4,202,760 5/1980 Storey et al. .

OTHER PUBLICATIONS

Review of Hemodialysis for Nurses and Dialysis Personnel-pp. 68–70, Second Edition C. F. Gutch and M. H. Stoner The C. V. Mosby Co., St. Louis, 1975.

Primary Examiner—Houston S. Bell, Jr.
Attorney, Agent, or Firm—Schroeder, Siegfried, Vidas, Steffey & Arrett

[57] ABSTRACT

A proportioning system for preparing hemodialysis or hemofiltration solutions. The apparatus of the system is a specially plumbed tank containing a flexible plastic container which holds solution concentrate. Introduction of pressurized water into the tank outside the bag discharges concentrate and water through separate paths into a mixing chamber at a rate determined by the size ratio of narrow orifices in the respective paths.

13 Claims, 1 Drawing Figure

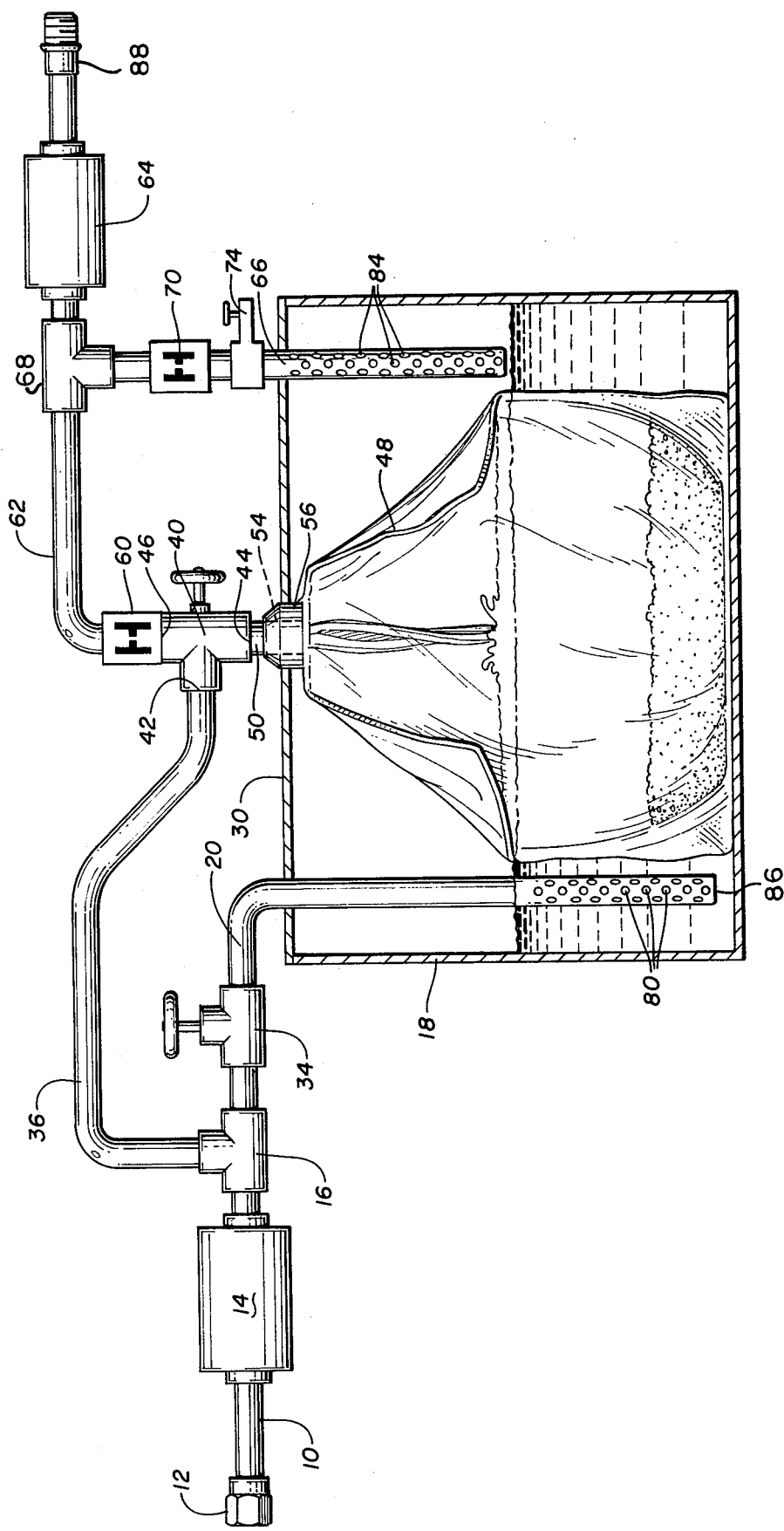

PROPORTIONING SYSTEM

DESCRIPTION

BACKGROUND OF THE INVENTION

Systems delivering dialysis solution to a hemodialysis unit are of three major types.

Batch type systems utilize a given volume of prepared dialyzing fluid in a tank. Fresh batches of fluid must be made as the fluid's waste removal capacity is exhausted. Where a small tank is used or where several dialyzers are supplied from the same tank, it is occasionally necessary to mix up two or more batches of solution before a dialysis run is complete.

Sorbent regenerative systems utilize a smaller volume of fluid which is cycled through a tube of absorbent material to remove waste from the fluid.

Proportioning systems continuously mix and deliver fresh fluid to the dialyzer. Such systems utilize a concentrate prepared in bulk which is then mixed in a predetermined ratio with water. Metering pumps and water-powered cylinders of fixed stroke are typically used to provide the correct proportion of water to concentrate. Electronic feedback systems, utilizing a conductivity meter to control a concentrate pump, have also been devised.

For batch or sorbent systems, it is possible to prepare dialysis solutions directly from dry reagents. This is unusual, however, since such preparation requires careful weighing of a number of ingredients, typically including sodium chloride, sodium bicarbonate or sodium acetate, potassium chloride, calcium chloride, magnesium chloride and lactic acid. Glucose or invert sugar may be added to adjust the osmolality of the solution to a desired level. Because of this complexity, most dialysis solutions are prepared from commercially supplied concentrate.

Proportioning systems require the use of some kind of a solution concentrate.

Preparation of dialysis solutions from concentrates, however, sometimes poses problems. Shipment costs for the concentrate are substantially higher than those of dry reagent. Large drums of concentrate may stratify, with the certain salts tending to layer out at the bottom. Furthermore, acetate, rather than bicarbonate, must be used as buffer because of the instability of bicarbonate. While this is not usually a problem since acetate is metabolized by the body to produce bicarbonate, some patients, particularly those with liver disease, cannot metabolize acetate ion.

SUMMARY OF THE INVENTION

The present invention relates to a proportioning system which may be used in hemodialysis systems or in other applications using dilute aqueous solutions such as hemofiltration systems. The system utilizes orifices of fixed size to regulate the flow rate of water and concentrate into a mixing chamber. A novel mechanism for maintaining equal pressure behind the orifices causes the respective flows of water and concentrate to be regulated solely by the size relationship of the orifices.

The apparatus of the present invention is a specially plumbed closed tank which holds a collapsible flexible container such as a thin wall plastic bag or diaphragm in which a predetermined amount of concentrate is contained. The tank is provided with a water supply connection on the exterior of the flexible container. The tank is also provided with two exit conduits, one from inside the flexible container and the other from outside the flexible container, each leading to the mixing chamber. The fixed size orifices are located in the exit conduits.

When the tank is filled by a combination of concentrate in the bag and water outside the bag, further introduction of water into the tank will simultaneously cause concentrate and water to be expelled from the tank through their respective exit conduits. Unlike mechanical devices such as pistons, the thin flexible container offers no significant frictional or other resistance to collapse. Therefore, pressure behind the respective water and concentrate orifices is equalized.

The preferred embodiment of the invention is adapted to permit preparation of dialysis solution directly from stable, dry reagents as well as from solution concentrate. Because solution can be prepared directly from dry reagents, the solution may contain bicarbonate rather than acetate buffer.

The flexible solute container may be manufactured as a disposable unit and sold with a predetermined amount of concentrate or dry reagents included therein. Such disposable units can minimize the hazards of technician error and save preparation time.

The apparatus of the present invention may be provided with a conductivity meter inserted in the path of the solution leaving the mixing chamber so as to allow the accuracy and precision of the solution to be monitored.

BRIEF DESCRIPTION OF THE DRAWING

The sole FIGURE shows a tank plumbed in accordance with the present invention. The tank and plastic bag contained therein are partially filled with water depicting an intermediate step in the operation of the device.

DETAILED DESCRIPTION OF THE INVENTION

The preferred embodiment of the proportioning system of the present invention is depicted in FIG. 1. Conduit 10 is connected by means of a fitting 12 to a source of water under pressure (not shown). For dialysis systems, the water supplied will typically have been purified by reverse osmosis, distillation, deionization or a combination of such procedures. The water is conveyed by conduit 10 to a pressure regulator 14 which maintains the water exiting therefrom at a predetermined constant pressure.

The exit flow from regulator 14 is divided by tee 16 into two separate paths. One path leads into tank 18 by a conduit line 20, passing into the tank through tank lid 30. A valve 34 in line 20 allows interruption of the flow of the water through the line.

The second flow path from tee 16 leads via conduit 36 to a three-way valve 40. Valve 40 has a first position which blocks all flow therethrough, a second position permitting flow between valve opening 42 and valve opening 44, and a third position permitting flow between valve opening 44 and 46.

The flow path for water between valve opening 44 and the interior of plastic bag 48 in tank 18 is provided by conduit 50 and hole 54 in seal member 56. Seal member 56 connects plastic bag 48, conduit 50 and lid 30 together. Member 56 is preferably made of plastic material to which bag 48 may be heat sealed. Adhesive or other means of sealing, however, may also be used.

Member 56 is also preferably detachably mounted, as by friction fit, to conduit 50 and in lid 30 so that the combination of member 56 and plastic bag 58 comprises an easily replaced disposable unit.

When valve 40 is in the third position, the solution may be directed out of bag 48, through narrow orifice 60 and conduit 62, to a mixing chamber 64.

Tank 18 has a water exit path formed by conduit line 66 which passes through lid 30. Conduit line 66 merges with conduit 62 at tee 68 so that water flowing out of tank 18 through conduit 66, and solution flowing out of bag 48 through conduit 62, are mixed together in the mixing chamber 64 to accomplish a solution dilution in accordance with the ratio of flow rates of the water and solution concentrate into the chamber.

Conduit line 68 includes a narrow orifice 70, similar to orifice 60, which restricts the flow of water therethrough. A vent 74, openable to the atmosphere, is also included on conduit line 66 between tank lid 30 and tee 68.

In the preferred embodiment, the terminal portions of conduits 20 and 66 extend into tank 18 a substantial fraction of the depth of the tank. These interior extension portions include a large number of holes 80 and 84, respectively, through the walls of said conduit proportions.

To prepare a solution from dry reagents, a predetermined amount of dry solute material such as sodium bicarbonate or a mixture of sodium bicarbonate and other dialysis solution ingredients is placed in bag 48. Bag 48 is collapsed by evacuation and connected by a member 56 to the tank lid and conduit 50. Tank 18 and lid 30 are then closed in water-tight sealed relationship. Vent 74 is opened to the atmosphere and the bag filled with water to dissolve the solute by opening valve 40 to its second position. As it is filled, the bag expands to the free volume of the tank, expelling air through the vent as it does so.

If the free volume of the tank is measured prior to filling, the concentration of the resulting solution after the bag is filled will be predetermined by the amount of solute originally introduced into the bag.

After the bag has filled the tank, vent 74 is closed, valve 40 is moved to its third position and valve 34 is opened to introduce water into tank 18 under a pressure determined by regulator 14. Upon entering the tank, the pressurized water may either exit the tank through the outlet provided by conduit 66 or it may displace solution in the bag, collapsing the bag and driving the solution through conduit 62 into the mixing chamber. So long as the bag does not offer significant resistance to collapse and the exit path through conduit 66 remains open, the flow rate of solution and water, respectively, into the mixing chamber 64 will be determined by the relative sizes of the narrow orifices 60 and 70. For a system utilizing 30 pounds per square inch water pressure, orifices 0.020 inches thick and having opening diameters therethrough of 0.029 inches and 0.140 inches, respectively, for the solution and water paths has proved useful in blending to produce an ultimate dilution of about 20:1 water to solution. The bag may be formed from 3 mil thick polyethylene.

If solution concentrate of appropriate concentration is used, the initial solute dilution within the bag may be eliminated entirely. In such cases, tee 16, conduit 36 and valve 40 are not necessary to the apparatus. Operation merely involves insertion of the bag into the tank, in connection with conduit 50, filling the tank with water and then continuing to introduce water into the tank as concentrate and water are expelled therefrom through orifices 60 and 70.

In the preferred embodiment, plugging of the tank exit by the expanded solution bag is avoided by placing conduit 66 somewhat inward of the sidewall of tank 18, providing the portion of conduit 66 which is inside tank 18 with a large number of holes 84 therethrough, and by partially filling tank 18 with a predetermined amount of water before filling bag 48. The bag is then filled until tank water first appears at vent 74, at which time filling is discontinued and the vent is closed. The FIGURE shows the bag partially filled after addition to the tank of a predetermined amount of water in accordance with this preferred method of operation. The concentration of the solution in bag 48 may still be determined because the volume of solution is that of the empty tank minus the volume of water initially added outside of the bag. This initial partial tank filling step may be accomplished by adding a measured amount of water to the tank before attaching lid 30, or by utilizing a metering device, not shown, in the water feedline formed by conduits 10 and 20.

Displacing conduit 66 somewhat inwardly from walls 18 provides an area between conduit 66 and the sidewall which will not be completely filled by bag 48 when a significant amount of water is already present in the tank. The holes on that side of conduit 66 will therefore always be unplugged thereby avoiding interruption of flow through conduit 66. A large number of holes should be provided through the walls of conduit 66 so that, even if partially plugged by bag 48, the total opening volume into conduit 66 will be substantially larger than that of orifice 70 so that orifice 70 remains the only significant flow restriction in the tank exit path formed by conduit line 66.

Partially filling the tank with water before filling the bag accomplishes a second beneficial object. The body of water reduces stretching stresses on the partially filled bag caused by gravity. Such stresses could cause weakening and breakage of the thin wall plastic bag or in the event of stretching a volume change affecting the concentration of the dissolved solids.

Holes 80 near the terminal end of conduit 20 provide a large volume multi-directional opening to minimize the pressure head which would otherwise occur at mouth 86 of conduit 20.

The exit flow from the mixing chamber 64 is connected by a fitting 88 to the dialyzer solution feedline or to another proportioning system in which the solution may be further diluted or mixed with additional dialyzing solution ingredients.

A conductivity meter, not shown, may be interposed in the flow path downstream from mixing chamber 64 to monitor the conductivity of the resulting solution and provide assurance of the precision and accuracy of the dilution.

By another variation, only some of the requisite dialysis reagents would be contained in the plastic bag. The orifices would be sized to accomplish only a partial dilution. This concentrate could then be combined with a concentrate of the remaining reagents from another source, such as a second unit of this invention, to produce the dialysis solution. This method may be necessary when using bicarbonate buffer as calcium sometimes precipitates from concentrated solutions containing sodium chloride, bicarbonate and lactic acid.

By yet another variation, the invention may be used to provide a source of standard concentrate which can then be fed into proportioning systems on existing dialysis units.

The system of the present invention may also optionally be provided with a drainage hook-up to the tank for emptying the tank between runs and a filter in the concentrate exit conduit upstream of orifice 60.

We claim:

1. Apparatus for preparing hemodialysis and hemofiltration solutions comprising:
   (a) rigid container having a first predetermined volume and having a closure means for providing a pressurizable cavity;
   (b) first, second and third conduit means extending into said cavity, said first conduit means adapted to be joined to a source of pressurized water, and including a pressure regulation means, said second conduit means providing an overflow exit for said cavity and said third conduit means extending through said closure means in sealed relationship with a flexible walled closed plastic container inside said rigid container and providing the sole inlet and outlet to the interior of said plastic container, said plastic container containing a dialysis solute and positioned and arranged so that the water external to said plastic container is isolated from the inside of said plastic container;
   (c) first and second orifice means positioned in flow controlling relationship in said second and third conduit means respectively; and
   (d) means joining said second and third conduit means downstream of said orifice means, whereby when water under pressure is introduced into said cavity through said first conduit means said flexible plastic container containing dialysis solute collapses inducing flow of said solute through said third conduit means and water through said second conduit means pass through said second and first orifice means respectively proportioning said water and dialysis solute and mixed in a mixing chamber to produce a dialysate of the desired concentration.

2. An apparatus as in claim 1 wherein said flexible plastic container is replaceable.

3. An apparatus as in claim 1 further comprising means for filling said plastic container to a predetermined volume.

4. An apparatus as in claim 3 wherein said plastic container filling means includes fourth conduit means in sealed relationship with said flexible plastic container and joined to a source of water.

5. An apparatus as in claim 4 wherein said flexible container filling means further comprises valve means interposed between said flexible plastic container and said third and fourth conduit means, said valve means having a first position prohibiting flow of water therethrough, a second position permitting flow of water from said fourth conduit means into said flexible plastic container and a third position permitting flow of water-dialysis solute mixture to flow from said plastic container into said third conduit means.

6. An apparatus as in claim 1 further comprising means downstream of said joining means for continuously monitoring the conductivity of the dialyzate produced.

7. A method for producing solutions of predetermined concentration comprising:
   (a) filling a rigid tank of predetermined volume having a flexible plastic container therein, said flexible container containing a predetermined volume of solution concentrate, with water to displace remaining air within said tank;
   (b) closing said tank to the atmosphere when said tank is full;
   (c) introducing further water into said tank;
   (d) simultaneously providing exit paths for water from said tank and concentrated solution from said plastic container as further water is introduced into said tank, collapsing said flexible container inducing concentrated solution flows, said exit paths including narrow orifices of predetermined size such that the relative exit flow rates of water and solution are determined thereby; and
   (e) merging said water and solution exit paths so as to cause mixing of said water and solution thereby to form a relatively more diluted solution of predetermined concentration.

8. A method of producing hemodialysis and hemofiltration solutions comprising:
   (a) filling a flexible plastic container within a rigid tank of predetermined volume, said plastic container containing a predetermined amount of solute material, with water to displace the air volume within said tank and dissolve said solute;
   (b) closing said tank to the atmosphere when said plastic container is displaced all the air within said tank;
   (c) introducing further water into said tank;
   (d) simultaneously providing exit paths for water from said tank and concentrated solution from said plastic container as further water is introduced into said tank, collapsing said flexible container inducing concentrated solution flow, said exit paths including narrow orifices of predetermined size such that the relative exit flow rates of water and solution are determined thereby as further water is introduced into said tank; and
   (e) merging said water and solution exit paths so as to cause mixing of said water and solution thereby forming a relatively more diluted solution of predetermined concentration.

9. A method as in claim 8 further comprising the step of introducing a predetermined volume of water into said tank prior to filling said flexible plastic container.

10. A method as in claim 7 or 8 wherein said method includes continuously monitoring the conductivity of the resulting dilute solution.

11. A method as in claim 7 or 8 wherein said solute includes a bicarbonate salt.

12. An apparatus as in claim 1 wherein said first conduit means is constructed and arranged so as to include a plurality of multi-directional holes at the terminal end.

13. An apparatus as in claim 1 wherein said second conduit means is constructed and arranged so as to include a plurality of multi-directional holes at the terminal end.

* * * * *

UNITED STATES PATENT AND TRADEMARK OFFICE
CERTIFICATE OF CORRECTION

PATENT NO. : 4,386,634
DATED : June 7, 1983
INVENTOR(S) : Peter Stasz et al

It is certified that error appears in the above-identified patent and that said Letters Patent are hereby corrected as shown below:

Column 3, line 15, delete "68" and insert - 66 -

Signed and Sealed this

Ninth Day of August 1983

[SEAL]

Attest:

GERALD J. MOSSINGHOFF

Attesting Officer           Commissioner of Patents and Trademarks